(12) United States Patent
Weingarden et al.

(10) Patent No.: US 12,133,865 B2
(45) Date of Patent: Nov. 5, 2024

(54) COMPOSITIONS AND THERAPIES USING NANODIAMONDS SUSPENDED IN A CARRIER

(71) Applicant: NANO MPI HOLDINGS, INC.

(72) Inventors: Marshall Weingarden, Milford, MI (US); Lyudmyla Derymedvid, Kharkov (UA); Wladimir Borodin, Kharkov (UA); Volodymyr Ivashchenko, Kharkov (UA); Andrey Factor, Farmington Hills, MI (US)

(73) Assignee: NANO MPI HOLDINGS, INC., Milford, MI (US)

( * ) Notice: Subject to any disclaimer, the term of this patent is extended or adjusted under 35 U.S.C. 154(b) by 616 days.

(21) Appl. No.: 17/401,589

(22) Filed: Aug. 13, 2021

(65) Prior Publication Data

US 2021/0369773 A1 Dec. 2, 2021

Related U.S. Application Data

(63) Continuation-in-part of application No. 17/012,649, filed on Sep. 4, 2020, now abandoned, which is a continuation-in-part of application No. 16/315,797, filed as application No. PCT/US2017/042786 on Jul. 19, 2017, now Pat. No. 10,894,060.

(60) Provisional application No. 62/363,915, filed on Jul. 19, 2016.

(51) Int. Cl.
| | |
|---|---|
| A61K 9/14 | (2006.01) |
| A61K 9/00 | (2006.01) |
| A61K 9/06 | (2006.01) |
| A61K 31/573 | (2006.01) |
| A61K 33/44 | (2006.01) |
| A61K 36/185 | (2006.01) |
| A61P 17/02 | (2006.01) |
| B82Y 5/00 | (2011.01) |
| B82Y 40/00 | (2011.01) |

(52) U.S. Cl.
CPC ............ *A61K 33/44* (2013.01); *A61K 9/0014* (2013.01); *A61K 9/06* (2013.01); *A61K 31/573* (2013.01); *A61K 36/185* (2013.01); *A61P 17/02* (2018.01); *B82Y 5/00* (2013.01); *B82Y 40/00* (2013.01)

(58) Field of Classification Search
None
See application file for complete search history.

(56) References Cited

U.S. PATENT DOCUMENTS

| | | |
|---|---|---|
| 7,294,340 B2 | 11/2007 | Sung et al. |
| 2007/0184121 A1 | 8/2007 | Sung |
| 2009/0220556 A1 | 9/2009 | Shenderova et al. |
| 2011/0008447 A1 | 1/2011 | Chao et al. |
| 2011/0307036 A1 | 12/2011 | Sung |
| 2015/0010631 A1 | 1/2015 | Getts |

FOREIGN PATENT DOCUMENTS

WO 2009/038850 A2 3/2009

OTHER PUBLICATIONS

International Search Report for PCT/US2017/042786 mailed Sep. 27, 2017 (1 Page).
Sea Buckthorn Oil, About Sea Buckthorn, Apr. 1, 2012 [retrieved on Sep. 13, 2017]. Retreived from the Internet: <URL: https://web.archive.org/web/20120401162025/http://sea-buckthorn-oil.com/about-sea-buckthorn/>.
Abstract of "Nanostructured Carbon Materials for Catalysis", Philippe Serp and Bruno Machado, Royal Society of Chemistry, 2015 RSC Catalysis Series No. 23, Print ISBN: 978-1-84973-909-2.
Abstract of Mochalin, Shenderova, Ho and Gogotsi, "The properties and applications of nanodiamonds, Nature Nanotechnology", vol. 7, Jan. 2012, p. 11.
Marty O. Visscher, et al; title: Quantitation of Epidermal and Mucosal Tissue Injury Using Contrasts Agents and maging Techniques ; Skin Res Technol. May 2009; 15(2): 180-186. (Year: 2009).
Rianna; title: Benefits of Sea Buckthorn Berry Oil for Skin; Jun. 1, 2015. Downloaded from https:// www.organictogreen.com/blogs/beauty-tips/57972355-benefits-of-sea-buckthorn-berry-oil-for-skin on May 6, 2020. (Year: 2015).
Geetha S, et al; title: Anti-oxidant and immunomodulatory properties of seabuckthorn (*Hippophae rhamnoides*)—an in vitro study; Journal of Ethnopharmacology, Feb. 28, 2002, vol. 79, No. 3, pp. 373-378. (Year: 2002).

*Primary Examiner* — Jake M Vu
(74) *Attorney, Agent, or Firm* — Fitch, Even, Tabin & Flannery, LLP

(57) ABSTRACT

A composition to treat epidermal insults may have an ungraphenated detonation synthesis nanodiamonds (UDSND) and medical grade Siberian Sea Buckthorn Berry Oil (SBB) composition in a blended uniform composition with 1% hydrocortisone cream; wherein the UDSND are at 2 nm to 4 nm in initial crystal size and in the range of 0.2% to 0.5% of the UDSND-SBB composition weight and the SBB which is 99.5% to 99.8% of the UDSND-SBB composition weight; and wherein total composition ratio is in the range of about 3:1 to 10:1 hydrocortisone cream to UDSND-SBB composition. Preferably, the total composition ratio can be about 6:1 hydrocortisone cream to UDSND-SBB composition.

9 Claims, 5 Drawing Sheets

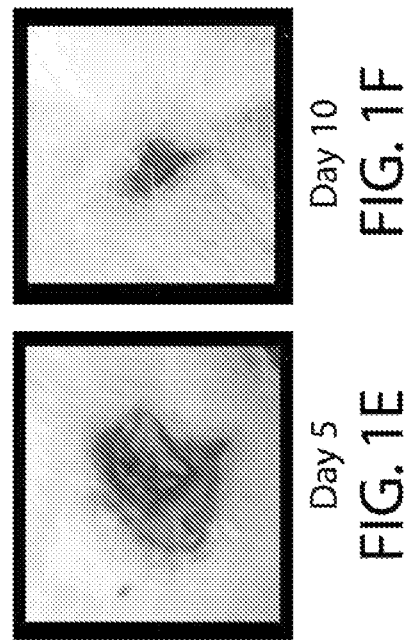

COMPOSITIONS AND THERAPIES USING NANODIAMONDS SUSPENDED IN A CARRIER

CROSS-REFERENCE TO RELATED APPLICATIONS

This application is a continuation-in-part of U.S. application Ser. No. 17/012,649, filed on Sep. 4, 2020, which is a continuation-in-part of U.S. application Ser. No. 16/315,797, filed on Jan. 7, 2019, which is a U.S. national phase application filed under 35 U.S.C. § 371 of International Application No. PCT/US2017/042786, filed Jul. 19, 2017, designating the United States, which claims priority from the U.S. Provisional Patent Application No. 62/363,915, filed Jul. 19, 2016, which are hereby incorporated herein by reference in their entirety for all purposes.

FIELD

Compositions and therapies using nanodiamonds are described herein and, in particular, compositions and therapies using nanodiamonds, for example, suspended in a carrier such as an oil or other liquid suspension, cream suspension or ointment suspension.

BACKGROUND

Partial treatments for burns or other disruptions to the epidermis, as well as partial treatments for arthritis and inflammation of ligaments and tendons or other soft tissues, and the like, have been developed in the art using drugs taken internally, drugs that are injected, and compositions applied as liquids, creams or ointments.

For example, oil squeezed from Sea Buckthorn berries ("SBB") can help revitalize skin and even to help heal wounds. The use of SBB oil can be a partial homeopathic remedy for burns and a variety of other issues. SBB oil is sold as an unregulated treatment that helps relieve the symptoms of rosacea, eczema, acne and dermatitis among other ailments. SBB oil should not be confused with Sea Buckthorn seed oil, which contains different nutrients and may provide different benefits to the body. SBB oil may be used as a partial homeopathic burn treatment and for other purposes, including ingestion as a treatment for gastric disturbances.

SBB oil contains a wealth of the nutrients, proteins, and essential fatty acids that may make skin healthy and strong. When applied directly to the skin, the oil may prevent the development of wrinkles and have an anti-aging effect on its appearance. Best of all, when the oil is absorbed into the skin, it may not cause drying like many moisturizing products and lotions. SBB oil may also partially shield the skin's surface from the ultraviolet radiation, thus acting as a low-level sun-block. SBB oil also carries anti-inflammatory agents that reduce disease, plus large quantities of skin-nourishing vitamins that may promote good health.

As mentioned above, one of the most fascinating abilities of SBB oil is its potential power to partially accelerate wound repair. Many types of skin damage, from cuts to burns, including radiation burns, may heal more quickly when treated with SBB oil. Many clinics have begun using it as a regular treatment because of its predictably good outcomes. Because SBB oil is so full of concentrated vitamins and omega fatty acids that may enhance skin growth, it can provide a perfect environment for scars and burns to get back to normal faster than untreated skin.

Researchers have even discovered that mice who were given SBB oil gained no weight, even when fed a high-fat diet. Potentially, essential fatty acids in the oil may be capable of programming the brain to discard unnecessary fat rather than store it.

Nanodiamonds were created in the 1960's in the Soviet Union and are known lubricants, conductors of heat and catalysis agents. More recently, internal uses for nanodiamonds, such as in combination with chemotherapy drugs, are being researched. (See generally, Nanostructured Carbon Materials for Catalysis, Philippe Serp and Bruno Machado, Royal Society of Chemistry, 2015; Philippe Serp and Bruno Machado, "Nanostructured Carbon Materials for Catalysis", Royal Society of Chemistry, 2015. (RSC Catalysis Series No. 23, Print ISBN: 978-1-84973-909-2); and Mochalin, Shenderova, Ho and Gogotsi, "The properties and applications of nanodiamonds, Nature Nanotechnology", Volume 7, January 2012, Page 11), and U.S. Pat. No. 7,294,340 for cosmetics.

Accordingly, while there have been advances in the art, further composition improvements and therapies are desired to improve the speed and effectiveness of treatment for various diseases and insults to a living body.

SUMMARY

Accordingly, exemplary compositions and therapies are provided herein and, in particular compositions including nanodiamonds, and in particular detonation synthesis nanodiamonds (DSND), are provided including methods of epidermal and subdermal therapies utilizing such compositions. It is noted that although detonation synthesis nanodiamonds are described herein as a preferred embodiment, other types of nanodiamonds created by alternate methods such as chemical vapor deposition, high-pressure high-temperature diamonds, laser energy, and the like could also be used within the scope of the present embodiments. It is noted that nanodiamonds produced by alternate methods to DSND do not have the active surface that plays a key role in accelerating and improving healing outcomes.

A composition to treat epidermal insults comprises suspended nanodiamonds. The nanodiamonds according to one approach are unagglomerated and ungraphenated detonation synthesis nanodiamonds at 2 nm to 4 nm in initial crystal size and concentration in the range of 0.2 composition weight % to 0.5% composition weight %, and preferably about 0.5%. The nanodiamonds may be suspended homogeneously in medical grade Sea Buckthorn berry oil. The nanodiamonds may be suspended in group consisting of Sea Buckthorn berry oil, Sea Buckthorn seed oil, glycerin, olive oil, Dimethyl sulfoxide (DMSO), hand creams such as those sold under the tradename UDDERLY SMOOTH and WORKING HANDS (e.g., Udderly Smooth, Working Hands), hydrocortisone cream, triple antibiotic cream, and combinations thereof. The nanodiamonds can be agglomerated crystals 30 nm to 50 nm in diameter and even larger, such as up to 100 nm.

According to one approach a composition to treat epidermal insults, is provided having nanodiomonds suspended in a composition selected from Sea Buckthorn berry oil, Sea Buckthorn seed oil, glycerin, olive oil, Dimethyl sulfoxide, hydrocortisone cream, triple antibiotic cream, polysporin, other topical antiseptics, and combinations thereof. The nanodiamonds may be suspended in Sea Buckthorn oil of the genus *Rhamnus*. The nanodiamonds may be formed by methods selected from the detonation synthesis, chemical vapor deposition, high-pressure high-temperature, laser energy, and combinations thereof. According to one approach the nanodiamonds are preferably detonation synthesis nanodiamonds. According to one approach the nanodiamonds may be agglomerated crystals 2 nm to 100 nm in diameter. According to one approach the nanodiamonds may be agglomerated crystals 30 nm to 50 nm in diameter. According to one approach the nanodiamonds may be 0.1% to 2% of total composition weight and/or the nanodiamonds are 2 nm to 4 nm. According to one approach the nanodiamonds are unagglomerated and ungraphenated detonation synthesis nanodiamonds 2 nm to 4 nm in initial crystal size and 0.2% composition weight, and wherein the nanodiamonds are suspended homogeneously in medical grade Sea Buckthorn berry oil.

According to one approach method of treating an inflammatory event or an injury event is provided by applying a composition to an area proximate to the inflammation or injury; wherein the composition comprises nanodiamonds and a carrier; and wherein the nanodiamonds have a concentration of about 0.1 to about 0.5% weight based on the total weight of the nanodiamonds and the carrier. According to one approach the carrier is Sea Buckthorn berry oil. According to one approach the carrier is an industrial hemp seed oil or CBD oil. According to one approach the carrier is glycerin. According to one approach the inflammatory event is associated with connective tissue. According to one approach the injury event is associated with an epidermal insult.

Another exemplary composition of the present embodiments may include a composition to treat neurological symptoms, comprising nanodiamonds suspended in a composition selected from the group consisting of hemp seed oil, Sea Buckthorn berry oil, Sea Buckthorn seed oil, glycerin, olive oil, Dimethyl sulfoxide, hydrocortisone cream, triple antibiotic cream, polysporin, other topical antiseptics, an industrial hemp seed oil, a CBD oil, and combinations thereof. The neurological symptom may be pain and in one embodiment the composition consists of nano diamonds and hemp seed oil.

Another exemplary composition of the present embodiments may include a composition to treat atopic dermatitis having a combination of Siberian Sea Buckthorn Berry Oil at 98.0 to 99.99 of total combination percent weight; and nano diamonds at 2.0 to 0.01 of total combination percent weight respectively. In one approach, the Siberian Sea Buckthorn Berry Oil may be 99.6 to 99.8 of total combination percent weight; and the nano diamonds may be 0.02 to 0.04 of total combination percent weight respectively. In another approach, the composition may have a range of 3-8 ml of the Siberian Sea Buckthorn Berry Oil and nano diamond combination per 59 ml of a cream having 2 percent hydrocortisone. In yet another approach the composition may have 5 ml of Siberian Sea Buckthorn Berry Oil and nano diamond combination per 59 ml of a cream having 2 percent hydrocortisone.

Another exemplary composition of the present embodiments may include an emulsified and sprayable composition to treat allergic rhinitis having a Siberian Sea Buckthorn Berry Oil and nano diamond combination and distilled water in the range of 40-60 total percent composition weight, wherein the Sea Buckthorn Berry Oil and nano diamond combination is 98.0 to 99.99 Sea Buckthorn Berry Oil total combination percent weight to 2.0 to 0.01 nano diamonds total combination percent weight respectively. In one approach, the Siberian Sea Buckthorn Berry Oil may be 99.6 to 99.8 of total combination percent weight; and the nano diamonds 0.02 to 0.04 of total combination percent weight respectively.

According to one approach, a composition to treat epidermal insults may have an ungraphenated detonation synthesis nanodiamonds (UDSND) and medical grade Siberian Sea Buckthorn Berry Oil (SBB) composition in a blended uniform composition with 1% hydrocortisone cream; wherein the UDSND are at 2 nm to 4 nm in initial crystal size and in the range of 0.2% to 0.5% of the UDSND-SBB composition weight and the SBB which is 99.5% to 99.8% of the UDSND-SBB composition weight; and wherein total composition ratio is in the range of about 3:1 to 10:1 hydrocortisone cream to UDSND-SBB composition. Preferably, the total composition ratio can be about 6:1 hydrocortisone cream to UDSND-SBB composition.

In this composition, the UDSND can be agglomerated crystals are in the range of about 30 nm to 100 nm in diameter. Alternatively, the UDSND can be agglomerated crystals are in the range of about 30 nm to 50 nm in diameter.

According to another approach, a composition to treat epidermal insults may include ungraphenated detonation synthesis nanodiamonds at 2 nm to 4 nm in initial crystal size and in the range of 0.2% to 0.5% of total composition weight suspended in medical grade Siberian Sea Buckthorn Berry Oil which is 99.5% to 99.8% of the total composition weight to for example, make 10 ml, and 2 oz. of 1% hydrocortisone cream to form a uniform composition.

According to this approach, the nanodiamonds can be agglomerated crystals up to 100 nm in diameter or about 30 to 50 nm in diameter. Also, the ungraphenated detonation synthesis nanodiamonds may be at 2 nm to 4 nm in initial crystal size are preferably about 0.5% of total composition weight of the UDSND-SBB composition weigh.

According to another approach, a method to make a composition to treat epidermal insults may include the steps of providing an ungraphenated detonation synthesis nanodiamonds (UDSND); providing medical grade Siberian Sea Buckthorn Berry Oil (SBB); blending the UDSND and SBB to form a UDSND-SBB composition wherein the UDSND are at 2 nm to 4 nm in initial crystal size and in the range of 0.2% to 0.5% of the UDSND-SBB composition weigh and the SBB which is 99.5% to 99.8% of the UDSND-SBB composition weight; and blending the UDSND-SBB composition to a uniform composition with 1% hydrocortisone cream, wherein total composition ratio is in the range of about 3:1 to 10:1 hydrocortisone cream to UDSND-SBB composition.

Other aspects and features of the embodiments herein will become apparent to those ordinarily skilled in the art upon review of the following description of specific embodiments in conjunction with the accompanying figures.

BRIEF DESCRIPTION OF THE DRAWINGS

FIGS. 1A-1F illustrate pathology tests of the condition of damaged skin of test animals at the 5th and 10th day of the experiment in: a control (FIGS. 1A and 1B respectively); with Sea Buckthorn Berry Oil only (FIGS. 1C and 1D respectively); and with Sea Buckthorn Berry Oil and DSND (FIGS. 1E and 1F respectively).

DETAILED DESCRIPTION

Figure 2:
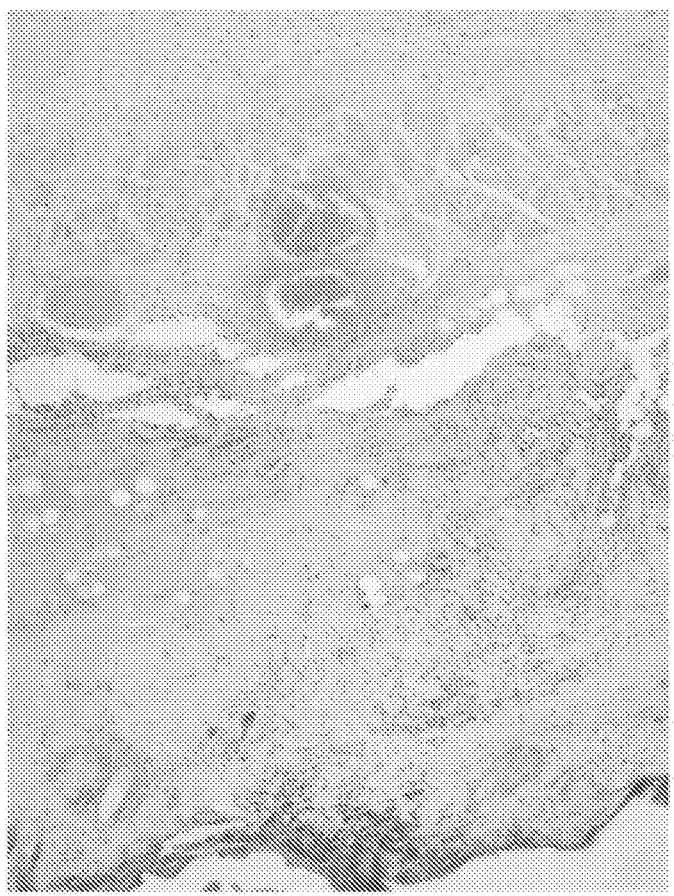
FIG. 2 illustrates the deep destructive changes of the skin, subcutaneous tissue and muscle layer of untreated rat control group on the fifth day.

Compositions and therapies using nanodiamonds, and in particular detonation synthesis nanodiamonds, combined with a carrier such as natural oils, and the like, are provided herein, including methods of accelerating and improving epidermal and subdermal therapies utilizing such compositions.

In the present embodiments, topical application of ungraphentated detonation synthesis nanodiamonds (also called "Ultra Dispersed Diamonds") (hereinafter "DSND" or "nanodiamond") suspended in a compatible carrier are used to facilitate repair of cutaneous assaults (defined further below) as well as address subdermal disturbances (defined further below). In the present embodiments, the blending or mixing of DSND into creams, ointments, liquids, powders or tablets and the like and combinations thereof are shown to contribute to the effectiveness of these substances.

As used herein "cutaneous assaults" and "epidermal insults" include, but are not limited to, burns, cuts and scrapes, psoriasis, scleroderma. As used herein "subdermal disturbances" include, but are not limited to inflammation and/or injury of ligaments and tendons, e.g., arthritis. In certain embodiments, the composition is applied topically to a desired area. As used herein, "over-the-counter remedies" include, but are not limited to, hand or body creams as well as triple-antibiotic or hydrocortisone ointments.

In certain embodiments, the composition is formed in a manner to facilitate topical application. For example, the composition may be incorporated in a cream, lotion, paste, or bandage. In other embodiments, the composition may be formed in a manner to facilitate oral administration. For example, the composition may be formed in to a pill, tea, or any general ingestible form. Application of the carrier with nanodiamonds reduces the required effective amount. In other embodiments, the composition can be incorporated in to an aerosol, which may be useful in the treatment of burns and potentially to disorders of the lungs such as chronic obstructive pulmonary disease or idiopathic pulmonary fibrosis. In yet still other embodiments, topical application includes the use of a roller ball tip applicator.

Embodiments of the composition may be used in combination with existing medications for various conditions to utilize the catalysis properties of DSND to enhance effectiveness of over-the-counter. (See generally, Serp, Philippe and Machado, Bruno, "Nanostructured Carbon Materials for Catalysis", Royal Society of Chemistry, 2015. (RSC Catalysis Series No. 23, Print ISBN: 978-1-84973-909-2); and https://www.academia.edu/17779798/Effect_of_structure_and_surface_properties_on_the_catal       ytic_activity_of_nanodiamond_in_the_conversion_of_1_2-dichloroethane).

Use of the composition may improve healing time (for example, as little as one-half the normal healing period for second degree burns). Compositions comprising up to 100 μg/ml DSND typically do not induce significant toxicity on a variety of cells. For example, Huang et al. found no significant change in the expression of TNFα and Bcl-x genes after incubation with the acid purified NDs compared with controls" (genotoxicity). (See generally, The Biocompatibility of Nanodiamonds and Their Application in Drug Delivery Systems, Ying Zhu,[1] Jing Li,[1] Wenxin Li,[1] Yu Zhang,[1] Xiafeng Yang,[1,2] Nan Chen,[1] Yanhong Sun,[1] Yun Zhao,[2] Chunhai Fan,[1] and Qing Huang[1] Theranostics, 2012; 2(3): 302-312. doi:10.7150/thno.3627. http://www.ncbi.nlm.nih.gov/pmc/articles/PMC3326739/).

DSND can be incorporated in to existing products for epidermal and/or subdermal therapies for any of the aforementioned ailments to provide the benefits of DSND and thereby improve the efficacy of the therapies.

In certain embodiments, DSND may be combined with buckthorn oil, glycerin, or a carrier suitable for epidermal or subdermal use. Here, such combinations may be used to address any of the aforementioned epidermal disruptions and/or subdermal issues.

DSND may be utilized as a catalysis agent and/or an adsorbing agent, in accordance with an embodiment of the present invention. Embodiments of the present compositions and methods show significantly lower cost than traditional known commercial drug treatments and delivery systems. (See generally The Biocompatibility of Nanodiamonds and Their Application in Drug Delivery Systems.Zhu, Li, Zhang, et al. Theranostics, 12 Mar. 2012). In use, the present embodiments can relieve pain quickly due to surface charge interfering with natural pain signaling and/or inflammation reduction. Effective at relieving pain of TMD (jaw pain due to bite misalignment and/or inflammation). Long term application can produce complete healing of the inflammation. Application to painful sinuses relieves or stops the pain (although does nothing for the sinusitis). The present embodiment's Surface charge (which can be in the range of about −30 to −70 mV) appears to speed healing by increasing/amplifying the effect of the body's normal signaling system that directs healing to a specific area. Epidermal application over bruised areas cause the bruises to heal quickly. Healing action of the ND+SBB combination can also cause the body to repair old scars. Use of the ND+SBB on fresh burns/wounds causes them to heal without scarring. A limited varieties of facial discolorations may also be reduced using the ND+SBB combination. Special success has been achieved with "pregnancy mask". Either formula (ND+SBB or ND+glycerin) may will stop attacks of rheumatoid arthritis (RA), relieve or stop pain and also reduce swelling. Since RA is recurring, repeated applications may be needed for both prevention and to respond to new RA attacks (in the same area). The present embodiments can quickly heal cuts and scratches. Bleeding scratches can show visible healing in an hour.

Carrier

As used herein a "carrier" is defined as a material, or combinations of materials, into which DSND, or other type of nanodiamond, may be mixed, suspended or homogenized. The carrier may also be any existing material into which DSND can be homogenized to increase effectiveness.

In the present embodiments, preferred carriers are non-destructive and of a material into which DSND can be mixed or homogenized, preferably with ultrasonic mixing and, if liquid, one into which DSND that has 'fallen-out' (i.e. aggregated or left suspension) can be 're-homogenized' by a period of vigorous shaking, such as by hand for a period of less than one minute. Embodiments of the present compositions may include DSND suspended in an oil, cream, ointment or other carrier. For example, suitable carriers may include, but are not limited to, Sea Buckthorn Berry Oil, glycerin, DMSO, hand creams (e.g., creams sold under the tradename UDDERLY SMOOTH and WORKING HANDS), industrial hemp seed oil, CBD oil, and the like, and combinations thereof. Industrial Hemp Seed Oil is the oil pressed from the hemp seed which is not processed for food. CBD (Cannabidiol) is an oil derived from the cannabis plant.

Sea buckthorn berry (SBB) oil is the preferred carrier of the nanodiamonds of the present embodiment for the treatment of burns since SBB oil has its own healing properties. However, as mentioned above, other carriers may be suitable. For exemplary, and non-limiting, purposes, a topical application with nanodiamonds including glycerin (or a mixture of water and glycerin) as a carrier may be suitable for cuts, scrapes and other non-burn partial treatments and may be effective in treating subdermal conditions. Adding nanodiamonds to topical antiseptics, e.g., a triple-antibiotic ointment, or a corticosteroid cream or ointment are also effective for the treatments described herein. Glycerin and sea buckthorn berry oil have been tested successfully as carriers for sub-dermal inflammation and it is theorized that virtually any carrier without undesired side effects and that can hold/suspend nanodiamonds may also affect useful treatments, e.g., olive oil, DMSO, and a petroleum jelly sold under the tradename of VASELINE to varying degrees. However, as has been stated herein, the best treatments have resulted from the use of SBB oil as the carrier.

For example, when making DSND for use in lubricants, the DSND retains its graphene shell. When creating DSND for applications such as medicine or certain types of polishing or coatings, the DSND is refined extensively to remove up to 99.9% of impurities. The DSND that Nano Materials and Processes, Inc. produces for high purity applications such as medical is government certified to GOST standards as "food quality".

DSND has a combination of useful properties which are leveraged in the creation of our products. These properties include:

2-10 nm initial crystal size; aggregated size 30-50 nm;
~ 350 square meters surface area per gram;
MOH=10 (hardest material known);
Highly charged (active) surface, −30 mV to −70 mV;
Heat conductor;
Electrical insulator;
Adsorbs other materials (chemicals, impurities, drugs, etc.); and
Bactericidal
Anti-viral As shown below the properties of the DSND can enhance products under the following utilization matrix:

| Product | Crystal Size | Surface Area | Hardness (MOH = 10) | Surface Charge | Bactericidal | Heat Conductor | Electrical [1]Insulator | Adsorb |
|---|---|---|---|---|---|---|---|---|
| Lubricant additives | X | X | X | X |  | X | X | X |
| Lubricants | X | X | X | X |  | X | X | X |
| Fuel Additive | X | X |  | X |  |  |  |  |
| Polymers | X | X | X | X |  |  |  |  |
| Coatings, Chroming | X | X | X |  |  | X |  |  |
| Drug transport | X | X |  | X |  |  |  | X |
| Subdermal inflammations (e.g., arthritis, inflamed tendons/ligaments | X | X |  | X |  |  |  |  |
| Burn and Wound Treatment | X | X |  | X | X |  |  | X |
| Cosmetic applications | X | X |  | X |  |  |  | X |

Notes:
[1]Varies by type of diamond and how it is processed.

Nanodiamonds

Ungraphenated detonation synthesis nanodiamonds (DSND), as used in the compositions described herein, are carbon nanoparticles with a truncated octahedral architecture that are typically about 2 nanometers (nm) to 8 nm in diameter. This refers to initial crystal size. DSNDs may have an initial crystal size of 2 nm-20 nm without agglomeration. This is a function of the production parameters of the nanodiamond (ND). The ND agglomerates through covalent bonding and typically reaches about 30-50 nm in size. This can be reduced by further treatment, however, there may be some purity problems associated with doing so. The DSND used in the present embodiments typically are about 30-50 nm on average. Initial crystal size of DSND may be 2-20 nm with the possibility of creating even larger crystals, although these are usually produced by agglomeration of 2-10 nm DSND.

Detonation synthesis nanodiamonds ("DSND", also known as 'ultra dispersed diamond" or "UDD') are created by the explosion of TNT or RDX in a specially shaped, sealed chamber. The explosion creates the extremely the high pressure and temperature needed to form diamond crystals. The size of the crystals formed varies based upon the conditions of the explosive environment. The initial crystal size according to one approach is typically 2-10 nm.

DSND can be refined from the residue of the explosion and purified to the extent needed for a particular application.

Commentary of each product is as follows:

| Product Category | Commentary |
|---|---|
| Lubricant additive— Engine Oil | DSND delivers both protection of contacting metal surfaces and improved performance and extended life of the resident lubricant. The core protection is delivered over time as DSND crystals become a part of the metallic lattice, creating a DSND coating that is not only the hardest known and therefore wear resistant, but also one that incorporates its own lubricity by adsorbing the native lubricant on its surface protecting against loss of lubrication conditions. This applies all contacting metal surfaces such as engine components, gears, worm drives, bearings, etc. DSND improves the characteristics of the native lubricant. First, while oil is a heat insulator, DSND is an excellent heat conductor both lowering and stabilizing operating temperature and delivering faster cooling on shutdown. Second, DSND makes the native lubricant more elastic, reducing the effect of reduced lubrication conditions. Third, it suppresses the formation of soot from fuel combustion, the major enemy of the oil additive package, extending the life of engine oil by up to 2-1/2X; it has been known to clean carboned-up engines and drastically improving fuel economy (does not apply to "clean" engines). |
| Lubricant Additive— | DSND has been incorporated into grease and lubricating oils. |

-continued

| Product Category | Commentary |
|---|---|
| Other | The core protection is delivered over as DSND crystals become a part of the metallic lattice, creating a DSND coating that is not only the hardest known and therefore wear resistant, but also one that incorporates its own lubricity by adsorbing the native lubricant on its surface protecting against loss of lubrication conditions. This applies all contacting metal surfaces such as engine components, gears, worm drives, etc. Especially notable are the effects realized by addition to cutting fluid. Tool life is extended, cutting speed is increased improving process throughput and vibration is reduced improving cut accuracy (especially useful in precision cutting such as medical tools). |
| DSND Lubricants (oil, grease) | For sports equipment such as skate boards, roller blades and bicycles our nanodiamond lubricating oil gives new life to worn bearings and extends the life of new ones. Even worn rollerblade bearings pass the "spin test" when treated. Treat bicycle bearings, chains, etc. with oil to reduce friction and extend life. Use oil on anything where you would normally use lubricating oil Where dissimilar metals are used in a product that can result in galvanic corrosion, use DSND oil not only as a lubricant but to reduce or eliminate corrosive damage. Use grease on bearings, CV joints, etc. to improve lubrication effect and extend contacting surface life. |
| Fuel Additive | Fuel Additive-CC ™ has been tested in gasoline and diesel fuels. In gasoline a fuel economy increase of 7% was measured. In diesel fuel a fuel economy increase of 32.4% was measured. In addition there were significant reductions of undesirable combustion by-products such as NOX (>30%), hydrocarbons and soot (estimated 50%). Reduction in soot also reduces fuel consumption for regeneration of the diesel particulate filter (DPF) and reduces DPF maintenance cost. Add Diesel Fuel Additive-CC ™ in the proportion of 1.6 to 1.8 ml per gallon of diesel fuel. This can be added when refueling on the road, but it is best when added to a central fuel supply that serves multiple vehicles such as a local fleet (e.g., waste collection vehicle, snow plow, construction equipment). |
| Polymers | Add DSND to one or two-part epoxies (any cure method) to increase pull strength by more than 35%, deflection strength and quality of cure. Use it in combination with carbon fiber, bamboo, etc. to create materials with the strength of some metals (e.g., aluminum). |
| Coatings, Chroming | NMPI develops custom solutions that are added to existing chroming baths to add a nanodiamond layer on the surface of the metal. The MOH-10 nanodiamond surface improves the adhesion of additional coatings and for tools, dies or stamps can extend useful life by >40%. When used on tools and dies in a production environment it reduces the frequency of tool change, reducing costly downtime. |
| Drug transport | Current research shows that DSND is useful in the delivery of chemotherapeutics by using the adsorption property of DSND. The chemo molecule is attached to the DSND and the DSND readily penetrates barriers that currently restrict the chemo molecule alone. These include the root of certain tumors (e.g., glioma) and the blood-brain barrier. |
| Subdermal inflammations (e.g., arthritis, inflamed tendons/ ligaments | DSND in very low concentration is suspended in a carrier such as glycerin or hemp seed oil. When applied topically, the DSND quickly penetrates the skin to address the inflammatory condition to be treated. There are two observable effects. First, the activity of the charged surface of the nanodiamond interferes with the pain channel and may completely block the feeling of pain. Second, the DSND encourages the body's resources to repair the inflamed area; use over an extended period of time often leads to a partial or complete reversal of damage. This product has been used to ameliorate or ameliorate and correct pain in a variety of areas including hands, fingers, knees, feet, shoulders, spine and sinuses. |
| Burn and Wound Treatment | DSND in very low concentration is suspended in Siberian Buckthorn Berry Oil "SBB") which has known and significant healing properties. The active surface of the DSND accelerates the healing effect of the Siberian Buckthorn Berry Oil. The adsorb property of DSND carries SBB through the skin/wound to surround the affected area and deliver the SBB along with the accelerated healing effect contributed by the active surface of DSND so that healing is experienced around and through the entire burn/wound. In addition, the bactericidal property of DSND reduces the harmful activity of bacteria in the burn/wound area. A laboratory study by a university professor of dermatology shows that DSND accelerates healing over SBB alone by 17%. |
| Cosmetic applications | DSND in low concentration in Siberian Buckthorn Berry Oil "SBB") has been used to reduce or correct certain skin or complexion anomalies. One user reported the elimination of a six year old surgical scar on her hand after only a few applications. Another user reports the reduction of a "pregnancy mask" condition and also removal of certain facial blemishes. |

The present DSNDs not only exhibit various superior characteristics of diamond, such as chemical stability, and extremely high hardness, stiffness and strength, but also have the inherent advantages of nanomaterials, such as small size, large surface area to weight ratio, high surface activity derived from their local group and high adsorption capacity. Therefore, NDs have superior physical and chemical properties over conventional nanomaterials, as disclosed in the journal article The Biocompatibility of Nanodiamonds and Their Application in Drug Delivery Systems.Zhu, Li, Zhang, et al. Theranostics, 12 Mar. 2012, which is herein incorporated in its entirety. It is also noted that surface charge of the nanodiamond used in the present embodiments can be in the range of about −30 to −70 mV.

In another approach, individual ND crystal sizes provided in the present embodiments can have a diameter ranging from about 2 nm to about 100 nm. ND crystals can agglomerate to a diameter of about 30 nm to about 50 nm. While initial crystal diameter is 2-10 nm, the crystals agglomerate using covalent bonding into larger crystals in the range of 20-50 nm. The actual percentage of agglomeration and distribution of crystal sizes varies based upon the carrier used. The final crystal size can be determined by manipulation of the crystal so that greater than 90% of the crystals are in the size range of 30-50 nm. With additional processing the crystal size can be further reduced.

ND crystals have a plurality of desirable properties, including but not limited to, charged surfaces, high surface area, bactericidal characteristics, anti-viral characteristics, as well as an adsorb and hold the carrier/suspension to its surface allowing deeper transport and penetration into wounds. Accordingly, preferred initial crystals and agglomeration diameter allow for the greatest surface to volume ratio. ND concentration is also a factor in the effectiveness of the described treatments. For example, if the concentration is too low, there may not be enough surface area to transport effective volumes of the suspension into a wound, the surface available for catalysis is smaller and healing may be slower. In one approach healing power can be attributed to the carrier. In the case of SBB that is partially true for burns. However, for subdermal inflammations it appears that the healing power can derived from the ND itself as a catalytic agent.

If the concentration is too high, there may be no improved efficacy and depending upon the carrier, the crystals may agglomerate prior to being dispensed, reducing the total surface area available. The excessive concentration of ND may render them less effective because of interaction between charged surfaces as well as proximity that causes them to agglomerate. In the case of wound treatment, testing was conducted with a composition having a crystal concentration of about 0.01% to about 5.0%. Test results determined that a crystal concentration of about 0.2% resulted in the highest healing efficacy with a reduction in efficacy at percentages less than 0.2% and no additional benefit with percentages higher than 0.2%. The ability of ND crystals to remain in suspension varies by the type of carrier used such that the higher viscosity of the carrier the longer crystals remained suspended and with lower viscosity carriers the nanodiamond more readily returned to suspension using mechanical shaking while with more viscous carriers such as glycerin other means such as ultrasonic mixing is needed.

DSND are a class of carbon materials with catalytic properties related to their surface chemistry and electronic properties, as disclosed in Serp, Philippe and Machado, Bruno, "Nanostructured Carbon Materials for Catalysis", pages 54-56, Royal Society of Chemistry, 2015; and V Dolmatov, Yu, "Detonation synthesis ultra-dispersed diamonds: properties and applications", Russian Chemical Reviews 70 (7) 607-626 (2001), which are both herein incorporated by reference in their entirety.

Relevant properties of nanodiamonds include the ability to (a) adsorb impurities on their surface (similar to activated charcoal) to partially remove some impediments to healing; (b) act as a catalyst to enable natural processes to function more quickly or to function where they did not function previously; (c) adsorb the carrier in which they are suspended and deliver the carrier on and through the epidermis so that both the nanodiamond and the carrier reach affected areas beneath the epidermis; and (d) act as a bactericide or anti-viral.

Research by Zhang et al. (referenced above) indicates that in comparison with carbon nanotubes and graphene, DSND had the highest cellular uptake rate. In general, DSND crystals may be taken into cells via a clathrin-mediated endocytosis pathway. In addition, the surface charge of DSND influences its cellular uptake. In certain embodiments, the composition can comprise, unagglomerated, ungraphenated DSNDs having an initial crystal diameter of about 2-4 nm, at 0.2% by composition weight and homogenized in (medical grade) sea buckthorn berry oil, which can be used to address any of the aforementioned epidermal insults. In another embodiment, the carrier can comprise sea buckthorn berry oil, glycerin, and/or DMSO, which can be used to address any of the aforementioned subdermal conditions.

The suitable range of DSND size is about 2 nm to about 100 nm with typical applications being about 30-50 nm in size. Although crystal sizes greater than 100 nm may exhibit some level of therapeutic success, though with DSNDs that large, it is expected to take a lengthier period of time to do so for a comparable level of healing or amelioration than with DSNDs that are less than 100 nm in diameter. The healing function is directly related to the available surface area. Larger crystal sizes exhibit exponentially smaller surface area reducing effectiveness.

The sorbent properties of carbon are well known and are exploited for the removal of inorganic and organic ions from liquids and gases. A common example is the use of activated carbon as a filtering material and as a treatment for the oral ingestion of poisonous substances. The adsorb properties of ND crystals exceed those of all other carbon sorbents due to its large surface area in proportion to its weight (~300 $m^2$/g for 5 nm crystals and potentially higher up to approximately 350 $m^2$/g), multi-functionality of surface groups and the ability to modify the surface to target specific ions. ND surface functional groups can be manipulated for desired chemical, physical and biological properties. These characteristics allow the nanodiamond surface to be viewed as an ideal carrier for various molecules or biological molecules and the delivery or removal of molecules in vivo and in vitro.

It is clear from the testing of the current DSND embodiments that the present compositions are effective in promoting healing to injuries that are epidermal or subdermal by applying the catalyst in an appropriate carrier to the epidermis. Similar findings may be shown for compositions used internally. Moreover, since the DSND is inert and considered neutral when ingested, it may be used internally in a carrier of choice that may or may not target a specific item (e.g., a stomach ulcer, an irritation of the small intestine, a brain lesion, etc.).

Thus, DSND may be used to treat epidermal insults that are treated medically. DSND may be used to treat epidermal insults that are treated homeopathically or with over-the-counter products. DSND may be used to treat subdermal issues treated medically such as arthritis, inflammation of joints, inflammation of tendons or inflammation of ligaments. The present nano diamond crystal have also been shown to block pain. This may be manifested in a reduction in pain or in the elimination of pain (in some cases the pain does not return). The present nanodiamond formulations are also effective in treating both headaches and migraine headaches. This typically involves a topical application over the spine on the back of the neck. It appears that nanodiamonds in any carrier will work. Exemplary studies have found efficacious results with glycerin and/or industrial hemp seed oil as carriers, the former carrier having no additional medicinal properties. Additionally, the present nanodiamond formulations are effective in treating sinus headaches when applied over sinuses in forehead and/or below a user's eyes. The present nanodiamond formulations are effective in treating swollen glands such, as sub-maxillary glands with a topical application.

Siberian Sea Buckthorn Berry Oil with the present nanodiamond formulations are effective in causing the body to heal both recent and old scars (original finding based on a 6-year old surgical scar). It has also caused the disappearance of "pregnancy mask" in one subject. The present nanodiamond formulations are an effective treatment for atopic dermatitis with varying lengths of treatment depending upon duration of prior existence or severity. In one treatment approach Siberian Sea Buckthorn Berry Oil plus nanodiamond crystals was used. An efficacious treatment composition may include a composition of Siberian Sea Buckthorn Berry Oil and nanodiamonds. In one embodiment, the Sea Buckthorn Berry Oil/nanodiamond composition may be 99.6% to 99.8% Sea Buckthorn Berry Oil total composition weight to 0.04% to 0.02% nanodiamonds total weight respectively. In one embodiment 2 oz. (59 ml) of a cream is mixed with 0.169 oz. (5 ml) of the Siberian Sea Buckthorn Berry Oil/nanodiamonds composition for a total composition weight 2.169 oz. The cream may be selected from a list of hand creams such as those sold under the tradename UDDERLY SMOOTH and WORKING HANDS (e.g., Udderly Smooth, Working Hands), hydrocortisone cream, triple antibiotic cream, and combinations thereof.

Alternately, in another embodiment, the Sea Buckthorn Berry Oil/nanodiamond composition may be 98.0% to 99.99% Sea Buckthorn Berry Oil composition weight to 2.0% to 0.01% nanodiamonds total weight respectively. In addition to the 5 ml combination to 59 ml cream ratio/proportion, the combination to cream ration may also be in the range of 3-8 ml combination to 59 ml cream ratio/proportion.

In another embodiment, a topical nasal spray to treat allergic rhinitis can be added to distilled water, shaken prior to application for emulsification, and topically applied as a spray or mist. In one approach 5 ml of a combination of 99.6 to 99.8 Sea Buckthorn Berry Oil total weight percent to 0.04% to 0.02% nanodiamonds total weight respective can be added to 5 ml distilled water. The oil/nano diamond component and the water component can be a range of 40-60 percent weight water to 60-40 percent weight oil/nano diamond. Alternately, in another approach to this embodiment, the Sea Buckthorn Berry Oil/nano diamond composition may be 98.0% to 99.99% Sea Buckthorn Berry Oil composition weight to 2.0% to 0.01% nano diamonds total weight respectively. It is noted that ranges herein are provided for the components with the understanding that total of percent is 100 percent for each combination. Accordingly, as one component increases, the other component is respectively reduced to maintain a 100 percent total combination weight.

Long term use of nanodiamond treatment (e.g., topically applied glycerin plus nanodiamonds at 0.02% to 0.04% of total composition weight used to treat a user's runner's knee) unexpectedly resulted in a significant reduction in the user's serum cholesterol (from 212 to 184 md/dL) over the period of one year with application two to three times daily. The nanodiamond crystals adsorb fat molecules and are subsequently eliminated by macrophages.

The present Nanodiamond crystals may also be used as a chelation agent. According to one approach, a topical formulation of nanodiamond crystals at 0.02% to 0.04% of total composition weight plus, for example, hemp seed oil, typically without THC although CBD oil may also be used, and the like, and combinations thereof may be used. Also, IV infusion, or another forms of transdermal infusion, such as an adhesive patch are possible.

Compositions

The present composition embodiments, in general, suspend nanodiamonds in a carrier (which then can be applied to the skin with a neutral or added healing effect) so that the nanodiamond can provide improved and unexpected treatment results. The present embodiments demonstrate there is an effect from certain carriers being adsorbed on the surface of nanodiamonds and being more effectively delivered into the affected region and working more effectively in combination, e.g., corticosteroids or Siberian Sea Buckthorn Berry oil, or hemp seed oil. This effect has been demonstrated through the use of nanodiamond as a transport vehicle for chemotherapy agents such as doxorubicin, as the nanodiamonds can adsorb the chemotherapy molecule and then penetrate the tumor cell and remain within the cell far more effectively than the chemotherapy agent on its own.

Mixing/suspending and/or homogenization of nanodiamonds with a carrier to form the present embodiments may be accomplished using an ultrasonic homogenizer. Other types of mixers that may also be used singly or in combination include, but are not limited to: blade pressure homogenizer, (appropriately sized) ultrashear homogenizer, hydroshear mixer, French-press or Dounce Homogenizer. For all composition formations, the choice of mixer depends upon the percentage of de-agglomeration desired. De-agglomeration reduces the crystal size and increases the available surface area which increases the effectiveness of the same weight of nanodiamond on an exponential basis. Ultrasonification is one of the preferred methods. Use of a high shear mixer in conjunction with ultrasonification is a preferred technique. Nanodiamond agglomeration creates vine-like connections that require substantial energy to break. While there are other methods, ultrasonification is the best commercial method as it delivers a high amount of energy while also being scalable.

In use, the frequency of application and volume of the present compositions varies with the condition treated. For example, according to one embodiment the composition can be applied up to 6 times per day for psoriasis. Larger nanodiamonds, unagglomerated (up to 10 nm) or agglomerated up to 999.9 nm may be considered in this instance (note: larger materials may not be of medical grade and will be less effective because the amount of active surface is reduced). In certain embodiments, the composition comprises NDs having a diameter of about 30-50 nm. In an embodiment, the composition can be applied topically one to four times in a twenty-four hour time period.

Nanodiamonds may be incorporated in a carrier at about 0.1% to about 2% of the composition's total weight (nanodiamond plus carrier) (e.g., 0.1% to about 2% total composition weight).

In one composition embodiment, 2-4 nm initial crystal size detonation synthesis nanodiamonds may be suspended in Sea Buckthorn Berry Oil (genus: *Rhamnus*). 2-4 nm initial crystal size detonation synthesis nanodiamonds may be suspended other oils as well. Other oils can include glycerin, hemp seed oil, olive oil or other oil in which it can be whipped.

As will be shown below, effectiveness of the compositions has been demonstrated as a burn treatment including a 40-rat study, providing a significant improvement in healing over Sea Buckthorn Berry Oil by itself.

The use of DSND in any of the applications, combinations of treatments, or as a standalone treatment in a composition described herein such as DSND and sea buckthorn oil or glycerin or hemp seed oil among many possibilities presents a low cost with minimal or no side-effects. It reduces healing time of second-degree burns by approximately half and can be expected to reduce the costs associated with length of treatment including, but not limited to services and medications, and lost time.

When DSND is combined with other products such as skin lubricants (including, but not limited to sea buckthorn oil or glycerin for example), DSND serves as a catalyst to speed healing or otherwise enhance the result of using the carrier in which DSND is included.

DSND may be combined with other products that serve as a carrier for DSND, in order to allow DSND to penetrate the epidermis for use in addressing subdermal insults such as arthritis, inflamed ligaments or inflamed tendons. DSND may be combined with other products that serve as a carrier for DSND in order to allow DSND to penetrate the epidermis for use in addressing muscle spasms including spasms of the diaphragm.

Test Results

By way of a specific example, the following are compositions comprising a DSND and a carrier as a burn treatment. In one study, the wound healing effect of a combination of Sea Buckthorn Oil and a Suspension of ultra-dispersed diamonds (i.e., nanodiamonds) was evaluated.

The ability of drugs for the topical treatment of wounds to accelerate the processes of epithelialization, granulation and contraction is an important indicator of pharmaco-therapeutic efficacy. To evaluate the wound healing properties of the ND, the model of a burn wound with wax was used.

The thermal tissue damage in the body causes chain reactions designed to restore the biological integrity and regeneration of the affected area.

Research Methodology

Burn injury was reproduced on 40 white rats weighing 260-300 g. The animals were divided into 4 groups of 10 animals each: Group 1—control (animals with natural healing); Group 2—animals treated with the SBB with DSND with agglomerated crystal size from 30-50 nm in the weight proportion of 0.2% DSND to total combined weight of SBB and DSND; Group 3—animals to which was applied sea buckthorn oil (OO) which is an analog for the pharmaceutical form, pharmacological action and indications for use; Group 4—the intact animal. In each group, 5 animals are used for monitoring and biochemical studies and 5 animals are used for histomorphological research.

In this experiment the nanodiamonds used were produced by SPE SINTA Ltd (Kharkiv).

Superficial burns were reproduced by the K. L. Bairy method (Professor of Pharmacology, Manipal University). Animals were anaesthetized using ketamine (100 mg/kg) and the coat was removed on one side. On the shaved skin a stencil with a window of 4 $cm^2$ was used to define a treatment area that would be identical on all animals. A third-degree class A (IIIA) burn was produced by filling the window with wax heated to 80° C. Afterward the wax set, the stencil and wax was removed.

Treatment was started after 24 hours and continued using a single application per day until complete healing was observed. Treatment was applied in a thin layer on the affected skin surface. Efficacy of treatment was assessed at 3, 5, 7, 9, 12, 15, 18, 21 and 24 days using indicators which included: the burn area, time until epithelialization begins (average period of time for each group until the scab is gone and the pink skin covers the area), and determine the degree of wound healing (%), which is calculated by the formula [7]:

$$\text{Degree of Healing} = \frac{\text{Area of Burn on First Day} - \text{Area of burn on the Day of Measurement}}{\text{Area of Burn on First Day}} \times 100\%$$

After sustaining the IIIA burn injury, the rats formed a dense crust of brown color with clearly defined edges in the zone of necrosis and inflammatory changes to surrounding tissues. FIGS. 1A-1F show the condition of the damaged skin of the test animals at the 5th and 10th day of the experiment. Burn healing dynamics of the rats' skin lesions are grouped as: (a) no treatment (Control Group) (FIGS. 1A-1B), (b) treatment with buckthorn oil only (FIGS. 1C-1D); and (c) buckthorn oil and ND (FIGS. 1E-1F).

Improved healing times are demonstrated in the rats treated with the combination of sea buckthorn oil and nanodiamond. When DSND is applied to the affected area, rejection of the scab began after 9 days while the average for the group was 14.8 days, which is 31.5% less than in the control group pathology ($\sigma \leq 0.05$) (Table 1). In animals treated with oil only ("OO") the epithelialization period was 17.2 days, and was significantly lower than in the control group pathology (less than 20.4% $\sigma \leq 0.05$) (Table 1). The period epithelialization for the group treated with ND was 14 days, 3.2 days less than OO. Thus, the results suggest that the OO and the ND contributed to reducing the healing time of wounds on by 6.8 and 4.4 days, respectively ($\sigma \leq 0.05$) (Table 1).

TABLE 1

The impact on the studied oils period of epithelialization (scab rejection) of burn lesions (M ± m; n = 5).

| Experimental Group | Number of Days |
|---|---|
| Control | 21.6 +/− 1.122 |
| ND | 14.8 +/− 1.828*/@ |
| OO (oil only) | 17.2 +/− 1.114*/@ |

Notes:
1 *significance relative to control group ($\sigma \leq 0.05$).
2. @ significance relative to reference drug-sea buckthorn oil ($\sigma \leq 0.05$).
3. n—The number of animals in the group.

For rats treated with DSND, a significant decrease in the area showing the burn was observed beginning on the 3rd day and continuing through complete healing. This compares to healing beginning on the $7^{th}$ day and completed on the $18^{th}$ day for the group treated with sea buckthorn oil only (OO). The healing rates are compared to the control group in Table 2 ($\sigma \leq 0.05$).

Full healing in the group of animals who were treated with the ND occurred on day 18 of the experiment; OO—21 days; in the untreated control group—24 days.

TABLE 2

The impact of oil only and oil + ND on the degree of healing in the rat burn model as compare to the control group (n = 5).

| Day of Observation | Degree of Healing (%) | | |
|---|---|---|---|
| | Control Group | Oil and ND (ND) | Oil Only (OO) |
| 3 | 37.1 | 48.4* | 37.1 |
| 5 | 42.6 | 63.5* | 53.15 |
| 7 | 44.7 | 78.4* | 64.4* |
| 9 | 56.1 | 89.2* | 80.3* |
| 12 | 63.95 | 96.0* | 87.3* |
| 15 | 78.25 | 98.2* | 92.75* |
| 18 | 90.3 | 100* | 97.25* |
| 21 | 98.4 | 100 | 100 |
| 24 | 100 | 100 | 100 |

Notes:
1 *significance relative to control group ($\sigma \leq 0.05$)
2. n—number of animals in the group The most rapid healing of burned area is observed in the treatment of burn wounds with the DSNDs. At all stages of wound care, suspended nanodiamonds significantly improves wound-healing properties of sea buckthorn oil. This is an especially big improvement in the rate of healing observed in the early stages, the stage of inflammation and regeneration, which ultimately affects the quality of wound healing. For example, on the seventh day the degree of healing of wounds treated with DSND exceeded that of the control group by 1.75 times and wounds treated with oil only (OO)—by 1.22 times. The time required for at least 90% wound healing in all groups exceeded 18 days; for the DSND treated wounds it was 9+ days; and for the OO treated wounds it was 14+ days.

Based on the measured results it can be concluded that the suspended DSNDs in size range of 30-50 nm and in 0.2% weight of the composition reduce the harmful effects of free radicals, optimize metabolism, stimulate repair processes, and accelerate the healing of burn wounds. Healing properties of nanodiamonds may be based on their abilities to quickly restore the necessary protective properties of damaged skin tissue and initiate the so-called regenerative processes. The illustrated use of the DSNDs as described above prevents inflammatory processes in the area of skin damage and stimulates the wound healing process.

On the 12th day of the experiment, the blood of experimental animals was studied to determine the amounts of lipid peroxide (LPO)—Rini Technologies malondialdehyde (MDA) and dendritic cell conjugate (DC). Also measured were urea, creatinine, and seromucoid[7]. The level of protein photo-colorimetric was determined by Biuret reaction using a set of reagents supplied by "Filisist-Diagnostics" (Ukraine).

As is known, a significant increase in blood content of methylsulfonylmethane (MSM) in different types of pathology is an unfavorable indicator because the degradation products of biopolymers. MSM compromises the physical and chemical properties of cell membranes and makes them more accessible to different kinds of damaging effects including the processes of lipid peroxidation (POL). About 80% of MSM are products of disturbed protein metabolism and tissue destruction. The level of MSM is now used as a criterion the degree of endogenous intoxication.

The level of the average molecular weight (MSM) was investigated using the spectrophotometer. The measurements were performed on a spectrophotometer SF-46 UV—light, wavelength—254 nm. The content of interleukins and tumor necrosis factor (TNF) in serum were determined by using an ELISA test kit from "Biokontur" (St. Petersburg, Russia) on an enzyme-linked immunosorbent analyzer.

The results are shown in Table 3.

TABLE 3

Indicators of lipid peroxidation and toxicity in the blood of burned animals when using OO and the ND versus intact and untreated control group (M ± m; n = 5).

| Group of Animals | Indicator | | |
| --- | --- | --- | --- |
|  | MSM | MDA, micromole/l | DC, micromole/l |
| Intact Control Group | 0.05 ± 0.001 | 2.664 ± 0.039 | 49.424 ± 0.335 |
| Control Group | 0.13 ± 0.003* | 5.546 ± 0.074* | 81.682 ± 0.327* |
| ND + Oil | 0.11 ± 0.002*/@ | 3.404 ± 0.114*/@ | 57.766 ± 0.797*/@ |
| Oil Only | 0.12 ± 0.004* | 3.934 ± 0.07*/@ | 62.9 ± 1.514*/@ |

Note:
*fairly intact relative to control ($\sigma \leq 0.05$);
@Significant relative to the burned control group ($\sigma \leq 0.05$);
n—the number of animals in the group;
MSM—average molecular weight;
MDA—malonic dialdehyde;
DC—diene conjugates.

A result of the burn insult is the systemic activation of lipid peroxidation which correlates with the severity of clinical manifestations of the burn, severity of cytolysis and autointoxication. On the 12th day of the experiment the burn injury in untreated animals was accompanied by a significant growth of MSM (2.3 times), MDA (2.1 times) and DC (1.7 times) compared to the intact control (Table 3) ($\sigma \leq 0.05$). The application of OO resulted in reduced rates of 7.5%, 29.1% and 22.9%, respectively, compared to the burned control group. In turn, the ND reduced the level of MSM by 17.2%, MDA—38.7% and 29.3% for DC (Table 3) ($\sigma \leq 0.05$).

The blood of animals examined contained indicators of protein metabolism. The results are shown in Table 4.

TABLE 4

Indicators of protein metabolism in the blood of animals with burn injury using OO and the ND versus the intact and untreated control group (M ± m; n = 5).

| Study Group | Indicators | | |
| --- | --- | --- | --- |
|  | Total Protein | Urea | Seromucoid |
| Intact | 79.648 ± 0.897 | 7.748 ± 0.089 | 0.356 ± 0.015 |
| Control Group | 72.43 ± 0.616* | 14.764 ± 0.275* | 0.822 ± 0.026* |
| Oil with ND | 75.606 ± 0.725*/** | 9.744 ± 0.278*//* | 0.434 ± 0.014*//* |
| Buckthorn Oil Only | 76.998 ± 1.013*/** | 10.14 ± 0.365*//* | 0.616 ± 0.014*/** |

Note:
*fairly intact relative to control ($\sigma \leq 0.05$);
**Significant compared to burned animals ($\sigma \leq 0.05$);
n—the number of animals in the group.

The results indicate a reduction in total protein (9%) and increased levels of urea (90%) and seromucoid (130.8%) in the control group pathology (Table 4) compared to intact animals ($\sigma \leq 0.05$).

In the treatment of burns, the ND total protein level increased by 4.38%, OO increased by 6.3% compared to the untreated control; levels of urea and seromucoid declined for the application of the ND by 34% and 47.2%, and for the application of OO—by 31.3% and 25.5%, compared to untreated animals (table 4) ($\sigma \leq 0.05$). The results point to a normalization of protein metabolism, increasing its protein synthesis and reducing catabolism.

Next, the influence of the ND and OO on inflammation levels was investigated.

Macrophages play a significant role in the production of inflammatory mediators (e.g., TNF-$\alpha$, IL-1$\alpha$, IL-1$\beta$, IL-6, CRP). Results of anti-inflammatory cytokines (TNF-$\alpha$—tumor necrosis factor=TNF-$\alpha$—tumor necrosis factor; interleukins IL-1$\alpha$, IL-1$\beta$, IL-6=interleukins IL-1$\alpha$, IL-1$\beta$; C-reactive protein CRP=C-reactive protein CRP) are an important mechanism in the development of the response to the burn trauma injury. TNF-$\alpha$ typically initiates the cytokine cascade that leads to secondary cytokines [10]. Interleukin IL-1 is a pleiotropic cytokine that has a number of biological functions, including the regulation of inflammation and reaction affecting the maturation and activation of granulocytes, T and B cells. C-reactive protein, a fast acting sensor, reacts to inflammation from wounds including when receiving treatment. The level of C-reactive protein was measured by using test kits manufactured by Lachema™ (Czech Republic).

Test results show that the post-burn injury level of IL-1$\beta$ increased 3 times; IL-1$\alpha$—by 4.5 times; TNF-$\alpha$—by 1.9 times; and CRP—by 7.7 times compared to intact animals.

The use of DSND decreased the level of IL-1$\beta$ by 50%; IL-1$\alpha$—60%; CRP—by 67.8%; and TNF-$\alpha$—27.6%, demonstrates greater effectiveness compared to the OO treated group by 22.7%; 15.8%; 20.6% and 20.9% respectively ($r \leq 0.001$). This shows the involvement the anti-cytokine mechanism resulting from the DSND reparative effect.

tory markers compared to the control group: the level of IL-1p decreased 2.01 times; IL-1$\alpha$—2.5 times, CRP—3 times, TNF-$\alpha$—at 1.37 times; the ND performance exceeded the group treated with OO by 1.45 times; 1.4 times, 1.7 times and 1.3, respectively ($r \leq 0.001$).

On the basis of these results, OO and ND reduced the damaging effects of free radicals, optimized metabolism, stimulated repair processes, and accelerated healing of burn injuries in a statistically relevant manner.

2. Histologic study of healing action of the ND model on burn wounds http://stainsfile.info/StainsFile/stain/elastic/elasweig.htm Next, a histological study was under taken [5,6]. For histological studies of burned skin, the sample was fixed in 10% neutral formalin, then, pieces of skin with thickness of about 4 mm were taken. The material was wiped with alcohol and paraffin poured on it, producing slices of 5-6$\mu$ thickness. Preparations were stained with hematoxylin and eosin, used for general assessment of the tissue sample. Weigert's stain for elastic fibers preparation of resorcinol and fuchsine along with Weigert's stain method of Van Gieson for the detection and differentiation of connective tissue structures were employed. A McMannus' Periodic Acid Schiff's (PAS) reaction by (control of amylase) showed neutral glycosaminoglycans (GAGs).

All procedures with control animals and test animals in this experiment utilized decapitation performed under anesthesia in accordance with general ethical principles of experiments on animals (Ukraine, 2001), consistent with the provisions of the European Convention for the Protection of vertebrate animals used for experimental and other scientific purposes (Strasbourg, 1986) and the Helsinki declaration adopted by the General Assembly of the World medical Association (1964-2000 gg.), the Charter of the Ukrainian Association of bioethics and GLP standards (1992).

On the fifth day in the untreated control group, all the observations of the surface area of epidermal burns were usually bare except near the opening to the hair follicles. Separate islands of epidermis are not differentiated into layers and are characterized by severe degenerative changes

TABLE 5

Biochemical indicators of inflammation in the blood of animals with burns treated by either ND and OO (n = 5).

| Group | IL-1$\beta$ | IL-1$\alpha$ | TNF-$\alpha$ | CRP |
|---|---|---|---|---|
| Intact | 6.627 ± 0.286 | 2.38 ± 0.111 | 11.414 ± 0.273 | 0.564 ± 0.016 |
| Control | 21.156 ± 0.551* | 10.9 ± 0.355* | 27.528 ± 0.989* | 4.324 ± 0.166* |
| OO | 15.264 ± 0.388*/** | 6.126 ± 0.124*/** | 25.68 ± 0.31* | 2.384 ± 0.105*/** |
| ND | 10.494 ± 0.317*//* | 4.4 ± 0.062*//* | 19.932 ± 0.375*//* | 1.392 ± 0.101*//* |

Notes:
1. *significance relative to intact control ($\sigma \leq 0.05$);
2. **significance relative the burn control group ($\sigma \leq 0.05$);
3. ***significance relative comparator ($\sigma \leq 0.05$);

Evaluation of the results showed a significant increase in levels of inflammatory cytokines and CRP group compared with the control group of intact animals: the level of IL-1$\beta$ increased 3.2 times, IL-1$\alpha$—4.6 times, TNF-$\alpha$—2.4 times and CRP—7.7 times (Table 5) ($p \leq 0.001$), indicating the commencement of the inflammation phase and delay of healing. In this application, SBB reduced the healing time to varying degrees. As such, OO treatment reduced the level of IL-13-27.7%; IL-1$\alpha$—43.8%, CRP—47.2% compared with the control group ($r \leq 0.001$), TNF-$\alpha$ level decreased by 6.7% but the difference was not significant. Application of experimental ND oil significantly reduced the levels of inflammain cells. In 2 of 5 observations, the epidermis was almost completely absent except for islands of the epidermis, poorly defined, PAS-positive basal membrane in a thin discontinuous line; on the other over it missing.

The underlying tissues of the dermis, hypodermis, and muscle layer with severe destructive changes is shown in FIG. 2. The endothelium of the dermis, basal membrane with PAS reaction, and wall eosinophilic, homogeneous layers are not differentiated. FIG. 2 illustrates deep destructive changes of the skin, subcutaneous tissue and muscle layer of untreated rat control group on the fifth day. Sample is stained with hematoxylin and eosin and viewed at 100-X.

The zone of necrosis is separated from the underlying tissues at the wound edges and smallest area of demarcation of inflammation and swelling of blood vessel tissues. On the 10$^{th}$ day of the experiment, microscopic observations of the damaged zone reflected an absence of epithelial lining and a scab covering. The scabs contain pieces of necrotic epidermis, fibrin, numerous leukocytes and macrophages randomly arranged along with phagocytized bacterial colonies. The wound crust is defined by a narrow layer of fibrinous tissue necrosis.

After 21 days, observation reveals epithelization of the surface of the burned area, but in the central zone and at a considerable distance, the epithelial lining is crusted and covered with fibrin, necrotic scraps of fibrous structures and segmented leukocytes remain.

On the fifth day, in the second group of animals (treatment 00), destructive changes are observed including expulsion of the epidermis, dermis and, in 50% of the hypodermis and muscle tissue. The burn zone is devoid of epidermal lining other than in peripheral regions and the mouths of hair follicles. Under the epidermis necrotized dermis without differentiation for papillary and reticular layers. In the subject area, the damaged hypodermis and muscle layer tissues are visualized as stained masses.

At 10-days, the burned skin was covered by crust of uneven thickness in all observations. Under the crust is a zone of burn regeneration, growing a wide granulated layer of tissue. The top layer consists of a layer of evenly spaced, thin, newly formed blood vessels of about the same diameter. Towards the lower regions of the vessel nothing has regenerated and number of vessels are getting smaller and shrinking in size. Under the scab, the epidermis is regenerating as evidenced by cell hyperplasia. Here, the number of rows of cells reached 6-7.

Figure 3:
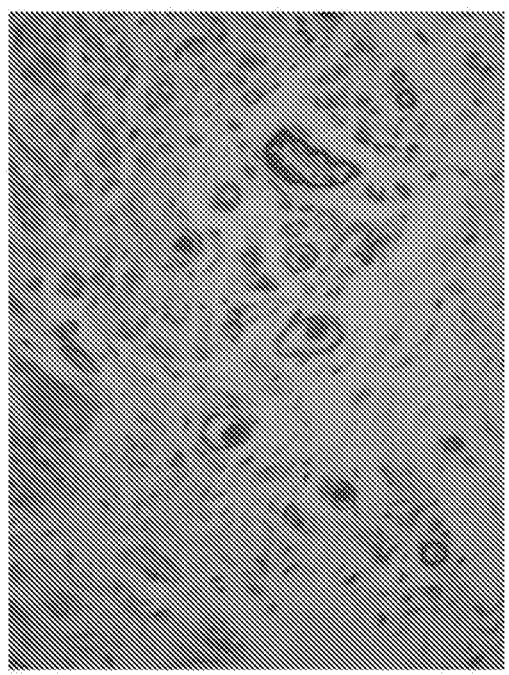
FIG. 3 illustrates the coarsening and thickening of the basal membrane of blood vessels in the deep parts of the area of regeneration in the second group of rats, $21^{st}$ day.

By the 21st day, regenerated epidermal areas are present, but central parts of all observations are still without epidermal lining and covered with scabs. Lower areas of the stained area include regenerated collagen fibers, which form bundles that are oriented parallel to the skin surface. Vascular basal membrane that is appears thickened, continuous, and PAS-positive (FIG. 3). FIG. 3. Illustrates coarsening and thickening of the basal membrane of blood vessels in the deep parts of the area of regeneration in the second group of rats, 21$^{st}$ day. PAS-reaction h400.

On the fifth day, the ND treated group showed destructive changes to epidermis, dermis and one-third of the hypodermis and muscle tissue. The epidermis in the burned zone appears as islands, local to the peripheral parts and near the mouths of damaged hair follicles. The zone of necrosis in eosinophilic stained presentation shows the detritus of fused together scraps of damaged fibrous structures. During the PAS reaction, the basal membrane of blood vessels is not defined. Necrotic tissue appears surrounded by a modified zone of peripheral inflammation.

Figure 4:
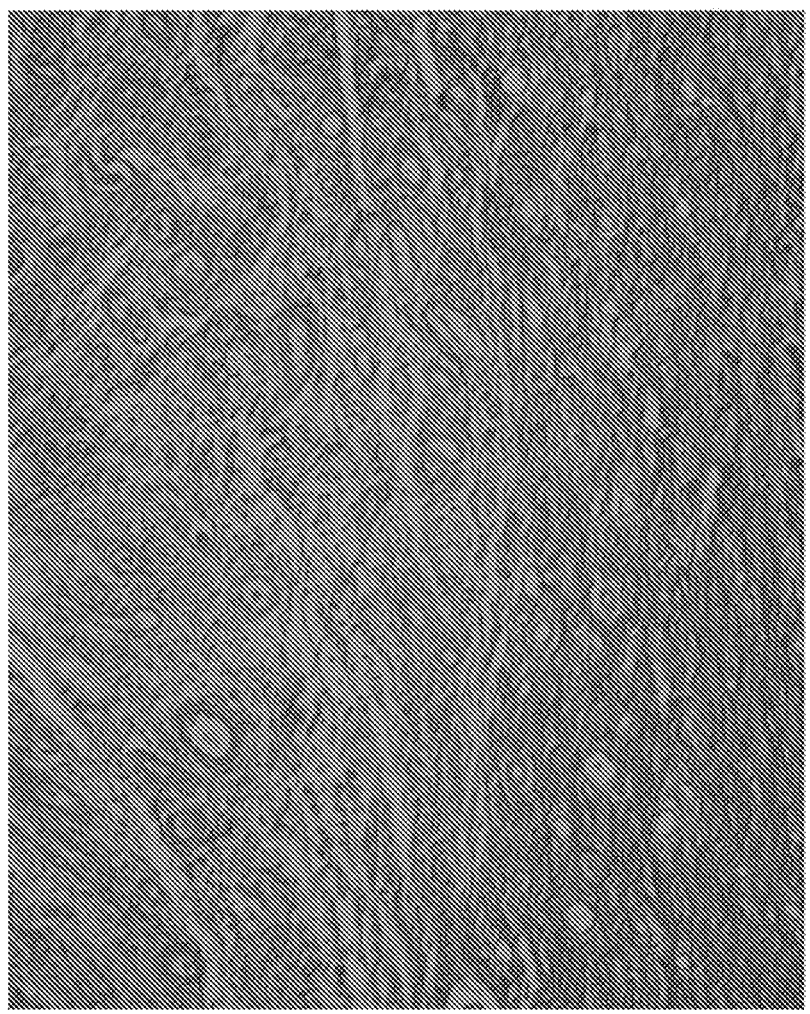
FIG. 4 illustrates the zone of regeneration, central and peripheral regions in the third group of rats, on the 10th day.

At the 10$^{th}$ day, burned skin in all observations appears covered by a crust of uneven thickness. Under the crust, a defined zone of regeneration a broad and expanding formation of granulation tissue. The central parts of the layer comprise a plurality of uniformly spread thin capillary vessels. (FIG. 4). FIG. 4. Illustrates a zone of regeneration, central and peripheral regions in the third group of rats, on the 10th day. The color of Weigert's stain method of Van Gieson, ×100.

At the edge of the regenerating area, the scab, in a small area can be seen the epidermis covering granulated tissue; cell hyperplasia in the area comprises six to eight rows of cells. In one of the five observations, the surface of the partially shed scab, having pus discharge, comprises randomly arranged, phagocytized bacterial colonies.

After 21 days, four of the five observed areas are covered completely with regenerated epidermis. In one observation, a small amount of pus can be observed. In two of the observations having fully a regenerated epidermis, an inflamed acanthosis is present, wherein the number of rows of cells have increased to five or six. The remainder of the epidermis shows a differentiation of the layers (basal, granular and spinous). Where the intensity of the PAS reaction of the epidermal basal membrane was continuous and moderate, area hyperplasia increased the intensity of the reaction.

Thus, the study arguably demonstrates the improved effectiveness and applicability of treatment of burn wounds using ultra-dispersed diamonds in combination with sea buckthorn berry oil as described herein.

Other Inflammatory Disease Treatment

As an extension of the results of the burn treatment experiment, ungraphenated dry nanodiamond material was mixed with glycerin for treatment of epidermal cracking, delivering improved healing. Epidermal cracks on fingers which were previously chronic with off-the-shelf treatments such as hand creams were healed in two to three days with the glycerin plus DSND treatment depending upon the severity of the crack in the epidermis. Based upon the success of the burn treatment and skin cracking treatment, the theoretical basis of nanodiamond operation was extended to other types of inflammatory disturbances.

A subject suffering from arthritic inflammation of the first joint of the ring finger was chosen as the test subject. The individual had a prior history of arthritic inflammation of said joint and successful early treatment of the condition with exercise. In this case, the individual had not treated the swelling for approximately four (4) weeks, an apparent spur in the joint developed and treatment with exercise was not successful. A glycerin and nanodiamond suspension was topically applied as a thin coating on the ring finger around the affected joint on a daily basis. Daily exercise using a grip strengthening device was continued. Arthritic pain was observed to subside in about eight (8) days. Over a period of eighty-three (83) days of treatment, arthritic swelling of the joint was statistically reduced, the joint reduced to normal size and the apparent bone spur ceased to manifest itself. Maintenance of the joint was continued using exercise only.

The nanodiamond and glycerin treatment was extended to inflamed ligaments in the right shoulder of the same subject. Treatment was topically applied daily to the epidermis of the desired area as a thin layer consisting of approximately 0.2-0.3 ml of the composition, which was sufficient to cover an area less than two (2) inches in diameter. The shoulder became asymptomatic in eleven (11) days and has remained so.

A composition of 0.2% DSND (based on the total weight of DSND and SBB) and SBB was used on the aforementioned subject to treat a historic case of epicondylitis in the right elbow that had remained untreated for forty-two (42) years. The composition was applied daily, in a thin layer (0.1 ml), on the epidermis in the area of the epicondyle. After fifteen (15) days, the symptoms were statistically reduced and were not observed to reoccur.

A composition having 0.2% DSND (based on the total weight of DSND and SBB) and SBB mixture was administered in a volume of approximately 0.4-0.5 ml to treat instances of knee pain/stiffness in both the left and right knees in the aforementioned subject. A composition having 0.2% DSND (based on the total weight of DSND and SBB) and SBB mixture was administered in a volume of approximately 0.1-0.4 ml according to another approach. The composition was (twice) applied daily to the knee area through the area of the attachment of the quadriceps. Initially, both knees were very stiff in the areas of the anterior cruciate ligaments, tendon of popliteus, ligament of Wrisberg, medial meniscus and the tibial collateral ligament and very difficult to flex. Twice daily treatment with the composition was extended to the epidermis over the affected areas of both knees. In addition, resistance exercise consisting of repetitive quadracep extensions was performed on alternate days. Statistical reduction of the symptoms were observed in about five days and nearly eliminated over the following thirty (30) days. It was recommended that application of the mixture and periodic exercise be continued until symptoms completely subsided.

Figure 5:
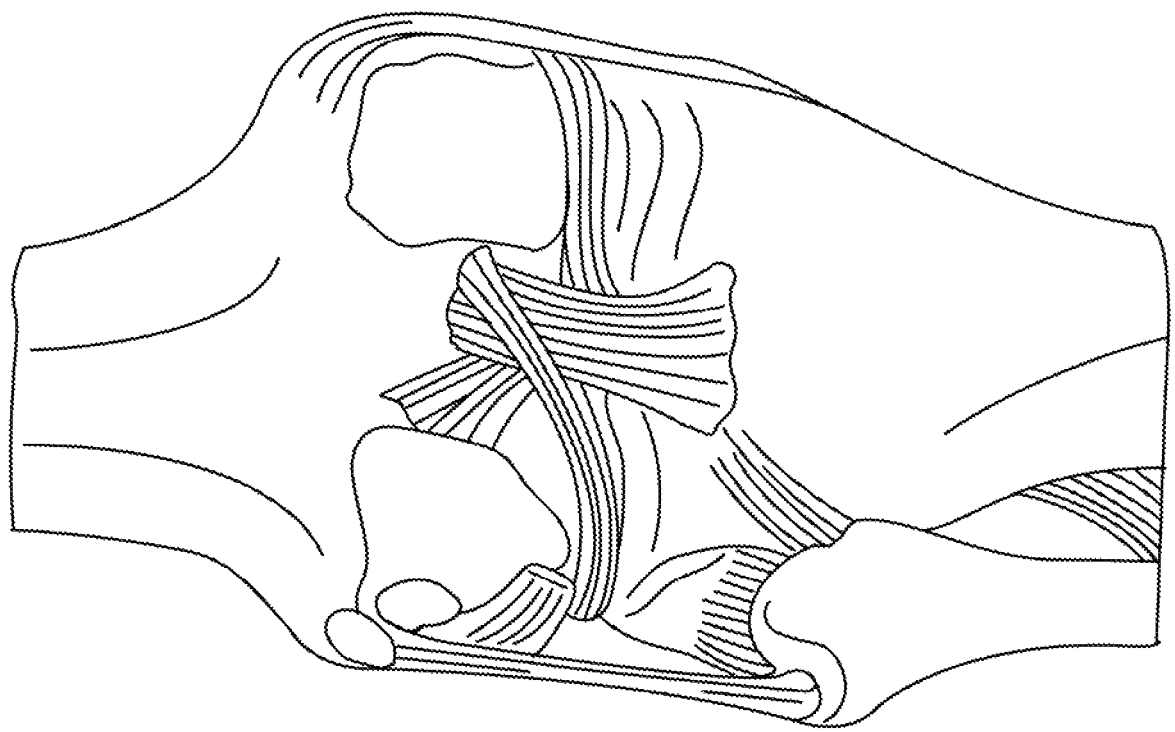
FIG. 5 is an illustration of a left knee-joint from behind, showing interior ligaments.

It is noted that time to relief using the embodiments presented herein appears to be dependent upon the severity of the inflammation, duration of the inflammation, the size of the affected area and the proximity to the surface of the epidermis and on the composition used. Treatment was made using two mixtures including 0.2% ND and 99.8% SBB by weight and 0.2% ND and 99.8% glycerin by weight. For example, if an arthritic inflammation is treated within two to three days of occurrence, pain relief was observed to occur within about one to two days and associated inflammation was observed to subside within seven days. For arthritic inflammation left untreated for more than two to three weeks, pain relief was observed to occur in about two to three days and the time required for inflammation and swelling to subside and potentially be reversed was at least four to twelve weeks. A similar response was observed for inflammations of tendons and ligaments. Further, a reduced relief and healing time was observed when the inflamed area is proximate to the point of treatment and required penetration by the ND is less than 0.5". Hence, the successful treatment of joints or ligaments/tendons with both a mixture of nanodiamond and glycerin and a mixture of nanodiamond and Sea Buckthorn Oil demonstrates that nanodiamond is the agent promoting healing. FIG. 5 Left knee-joint from behind, showing interior ligaments Henry Gray (1918) Anatomy of the Human Body.

According to another approach, ungraphenated detonation synthesis nanodiamonds (UDSND) and medical grade Siberian Sea Buckthorn Berry Oil (SBB) are combined to form a UDSND-SBB composition. In one example, UDSND at 2 nm to 4 nm in initial crystal size and in the range of 0.2% to 0.5% of total composition weight, and preferably about 0.5% of total composition weight, first suspended in SBB which is 99.5% to 99.8% of the UDSND-SBB composition weight. Next the UDSND-SBB composition is mixed into 1% hydrocortisone cream to form a uniform composition in a ratio of about 3:1 to 10:1 hydrocortisone cream to UDSND-SBB composition, preferably about 6:1 ratio of hydrocortisone cream to UDSND-SBB composition. The nanodiamonds can be agglomerated crystals 30 nm to 50 nm in diameter and even larger, such as up to 100 nm. The result compositions provide a powerful topical for skin issues, such as atopic dermatitis. According to another approach, 10 ml of the UDSND-SBB composition can be added to 2 ounces of hydrocortisone cream.

While the invention has been described in conjunction with specific embodiments, it is evident that many alternatives, modifications and variations will be apparent to those skilled in the art in light of the foregoing description. Accordingly, the present invention attempts to embrace all such alternatives, modifications and variations that fall within the spirit and scope of the appended claims. Throughout this specification and the drawings and figures associated with this specification, numerical labels of previously shown or discussed features may be reused in another drawing figure to indicate similar features. It is also noted that the attached list of Literature references following the Abstract and citations and other documents and URLs referenced are incorporated in their entirety herein by reference.

We claim:

1. A composition to treat epidermal insults, comprising:
an ungraphenated detonation synthesis nanodiamonds (UDSND) and medical grade Siberian Sea Buckthorn Berry Oil (SBB) composition in a blended uniform composition with 1% hydrocortisone cream;
wherein the UDSND are at 2 nm to 4 nm in initial crystal size and in the range of 0.2% to 0.5% of the UDSND-SBB composition weight and the SBB which is 99.5% to 99.8% of the UDSND-SBB composition weight; and
wherein total composition ratio is in the range of about 3:1 to 10:1 hydrocortisone cream to UDSND-SBB composition.

2. The composition of claim 1, wherein the total composition ratio is about 6:1 hydrocortisone cream to UDSND-SBB composition.

3. The composition of claim 1, wherein the UDSND are agglomerated crystals in the range of about 30 nm to 100 nm in diameter.

4. The composition of claim 1, wherein the UDSND are agglomerated crystals are in the range of about 30 nm to 50 nm in diameter.

5. A composition to treat epidermal insults, comprising:
ungraphenated detonation synthesis nanodiamonds at 2 nm to 4 nm in initial crystal size and in the range of 0.2% to 0.5% of total composition weight suspended in medical grade Siberian Sea Buckthorn Berry Oil which is 99.5% to 99.8% of the total composition weight, and
2 oz. of 1% hydrocortisone cream to form a uniform composition.

6. The composition of claim 5, wherein the nanodiamonds are agglomerated crystals up to 100 nm in diameter.

7. The composition of claim 5, wherein the nanodiamonds are agglomerated crystals 30 nm to 50 nm in diameter.

8. The composition to treat epidermal insults of claim 5, wherein the ungraphenated detonation synthesis nanodiamonds at 2 nm to 4 nm in initial crystal size are 0.5% of total composition weight.

9. A method to make a composition to treat epidermal insults, comprising the steps of:
providing ungraphenated detonation synthesis nanodiamonds (UDSND);
providing medical grade Siberian Sea Buckthorn Berry Oil (SBB);
blending the UDSND and SBB to form a UDSND-SBB composition wherein the UDSND are at 2 nm to 4 nm in initial crystal size and in the range of 0.2% to 0.5% of the UDSND-SBB composition weight and the SBB which is 99.5% to 99.8% of the UDSND-SBB composition weight; and
blending the UDSND-SBB composition to a uniform composition with 1% hydrocortisone cream, wherein total composition ratio is in the range of about 3:1 to 10:1 hydrocortisone cream to UDSND-SBB composition.

* * * * *